United States Patent [19]
Sambles et al.

[11] Patent Number: 5,598,267
[45] Date of Patent: Jan. 28, 1997

[54] OPTICAL SENSOR FOR ORTHOGONAL RADIATION MODES

[75] Inventors: John R. Sambles, Crediton; Guy P. Bryan-Brown, Heathfield, both of England

[73] Assignee: British Technology Group Limited, London, England

[21] Appl. No.: 384,591

[22] Filed: Feb. 3, 1995

Related U.S. Application Data

[63] Continuation of Ser. No. 261,306, Jun. 16, 1994, abandoned, which is a continuation of Ser. No. 110,842, Aug. 24, 1993, abandoned, which is a continuation of Ser. No. 807,838, filed as PCT/GB90/01128, Jul. 23, 1990 published as WO91/01489, Feb. 7, 1991, abandoned.

[30]       Foreign Application Priority Data

Jul. 21, 1989 [GB] United Kingdom ............... 8916764

[51] Int. Cl.$^6$ .................................................. G01J 4/00
[52] U.S. Cl. .......................................... 356/369; 356/445
[58] Field of Search .................................. 356/364–369, 356/301, 445, 370, 374, 128; 250/225, 237 G; 359/487, 488, 489, 566, 569–576, 245, 276; 385/2–4, 8, 141, 122

[56]               References Cited

U.S. PATENT DOCUMENTS

| | | | |
|---|---|---|---|
| 4,077,720 | 3/1978 | Kasai. | |
| 4,765,705 | 8/1988 | Seymour et al. | 359/566 |
| 4,889,427 | 12/1989 | Van Veen et al. | 356/445 |
| 4,948,225 | 8/1990 | Rider et al. | 385/122 |
| 4,997,278 | 3/1991 | Findan et al. | 356/445 |
| 5,116,121 | 5/1992 | Knoll et al. | 356/301 |
| 5,157,541 | 10/1992 | Schildkraut et al. | 385/4 |
| 5,229,833 | 7/1993 | Stewart | 356/364 |
| 5,255,075 | 10/1993 | Cush | 356/445 |

FOREIGN PATENT DOCUMENTS

| | | |
|---|---|---|
| 0242923 | 4/1987 | European Pat. Off. . |
| 3802538 | 8/1988 | Germany . |
| 8907756 | 8/1989 | Germany . |
| 2066458 | 7/1981 | United Kingdom . |
| 2153524 | 8/1985 | United Kingdom . |
| 8903055 | 4/1989 | United Kingdom . |

OTHER PUBLICATIONS

Journal of lightwave Technology, "Focussing Grating Couplers for polarization detection" vol. 6, No. 6, pp. 1028–1033, S. Ura et al.

Applied Optics, "Absolute S–and P–plane polarization efficiencies for high frequency holographic gratings in the VUV", vol. 20, No. 10, May 1981, Caruso et al, pp. 1764–1776.

Applied Optics, vol. 20, No. 10, 15 May 1981 (New York, N.Y. US) A. J. Caruso et al; "Absolute S–and P–Plane Polarization Efficiencies for High Frequent Holographic Grating in the VUV", pp. 1764–1776.

WO, A. 89/03055 (University of Strathclyde) Apr. 6, 1989, see p. 5, line 34, p. 6, line 6; claims 1–9.

Journal of Lightwave Technology, vol. 6, No. 6, Jun. 1988, IEEE (New York, N.Y. USA) S. Ura et al; "Focusing Grating Couplers for Polarization Detection", pp. 1028–1033, see pp. 1031–1032, FIG. 8.

WO A, 89/07756 (W. Lukosz) 24 Aug. 1989, see claims 15–23.

*Primary Examiner*—Hoa Q. Pham
*Attorney, Agent, or Firm*—Cushman, Darby & Cushman, IP Group of Pillsbury Madison & Sutro, LLP

[57]                ABSTRACT

An optical sensing device that incorporates either a surface plasmon-polariton or guided mode apparatus for converting radiation between s and p modes together with a sensor for detecting a maximum in conversion between the s and p modes.

39 Claims, 16 Drawing Sheets

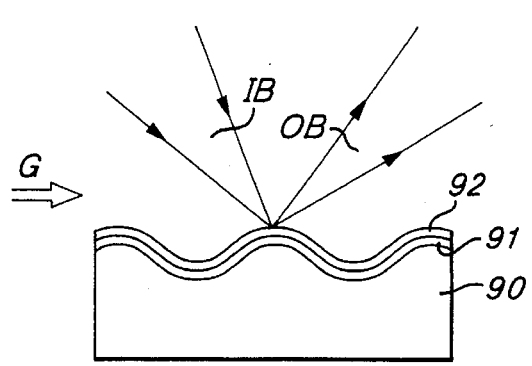
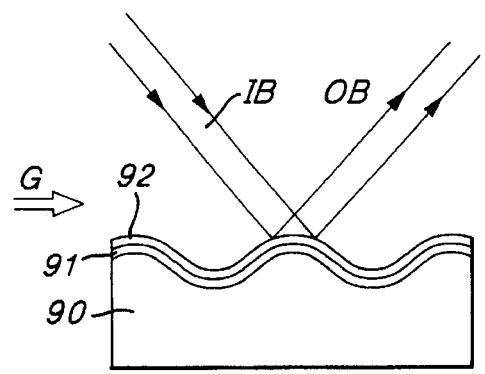
Fig. 9a          Fig. 9b
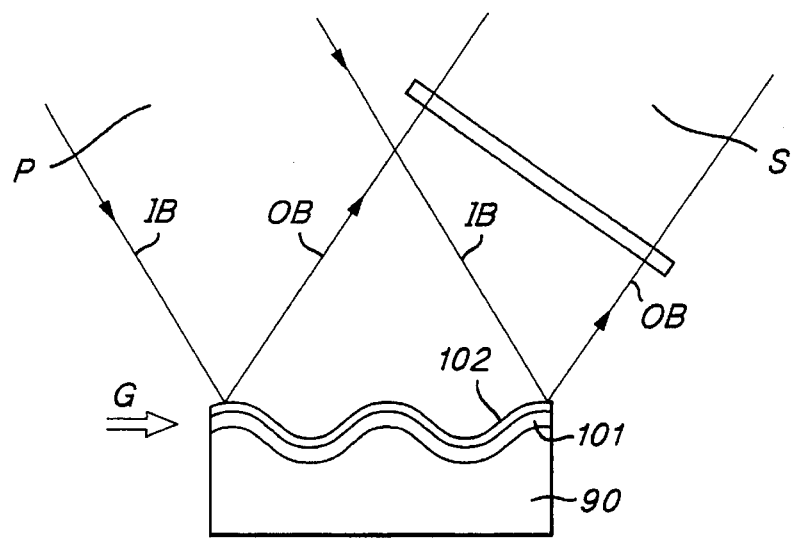
Fig. 10

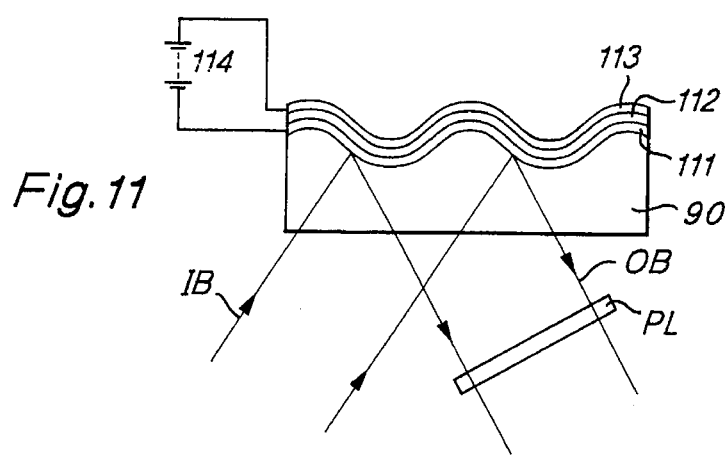
Fig. 11
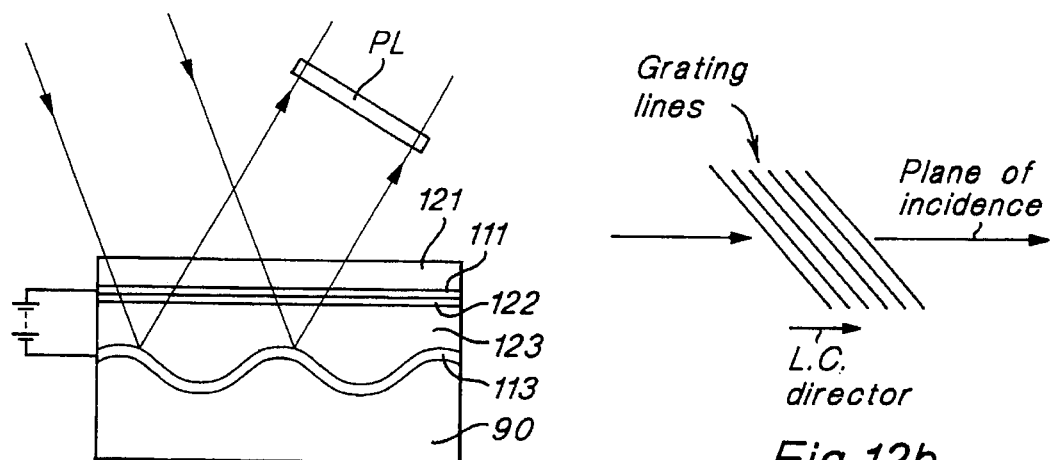
Fig. 12a
Fig. 12b
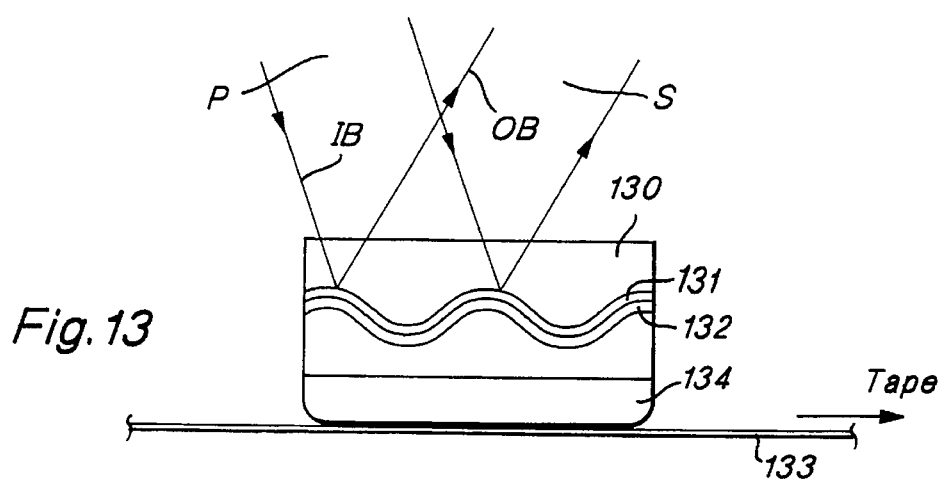
Fig. 13

OPTICAL SENSOR FOR ORTHOGONAL RADIATION MODES

This is a continuation of application Ser. No. 08/261,306, filed on Jun. 16, 1994, which was abandoned upon the filing hereof, which is continuation of application Ser. No. 08/110, 842, filed Aug. 24, 1993, which is a continuation of application Ser. No. 07/807,838, filed as PCT/GB90/01128, Jul. 23, 1990 published as WO91/01489, Feb. 7, 1991, both now abandoned.

BACKGROUND OF THE INVENTION

This invention relates to optical sensors and, in particular, to sensors based on the use of surface plasmon-polaritons (SPP) and guided modes for coupling orthogonal radiation modes.

SPP based optical sensors work on the principal of detecting changes in the SPP resonance as a thin layer on the metal which supports the SPP is changed in either dielectric constant or thickness.

In general there are two ways of monitoring SPP resonances (a) change in reflectivity as a function of angle of incidence (momentum of the photons)

(b) change in reflectivity as a function of wavelength (energy of the photons).

Typical devices use a grating coated in an opaque layer of gold or silver and the system is set so that the detector examines the edge of the resonance—the region of steepest gradient in R v. θ or R v. λ. Any shift in the SPP resonance is then recorded as a minimum in received intensity.

SUMMARY OF THE INVENTION

According to the present invention, an apparatus for sensing polarization conversion in a coating layer on a diffraction grating comprises means for illuminating the coating with radiation at a first polarization, the direction of polarization and the direction of the grating lines lying at an angle with respect to one another in the grating plane; means for receiving radiation reflected by the coating at a second polarization crossed with respect to the first polarization; and means for sensing a maximum of received radiation.

Optionally the polarization conversion is caused by surface plasmon polarization resonance, the coating is a metal coating, and the angle between the direction of the first polarization and the direction of the grating lines is 45°.

Optionally the means for illuminating the coating comprises a monochromatic source, and the means for receiving radiation is sensitive to the angular position of the received beam.

Alternatively, the means for illuminating the coating comprises a polychromatic source, and the means for receiving radiation is sensitive to the angular position of the received beam. As another alternative, the means for illuminating the coating comprises a polychromatic source, and the means for receiving radiation is wavelength sensitive.

Preferably there is also provided means by which a property of the coating of the diffraction grating is varied. The grating may be enclosed in a container through which a gas or vapor is caused to flow.

As another alternative, the polarization conversion is caused by a guided mode, the coating on the grating is a dielectric layer, and the angle between the direction of first polarization and the direction of the grating lines is greater than 45°, for example between 50° and 60°.

We have found that it is advantageous to construct devices based on a procedure which involves not the detection of an SPP resonance minimum but a maximum.

This is achieved by rotating the grating through 45° with respect to the plane of incidence and using crossed input and output polarisers.

An input beam having TM polarisation will then give zero output for a detector set for TE except when the angle of incidence (momentum) or wavelength (energy) corresponds to the excitation of an SPP on the grating surface. Because the grating grooves are at 45° to the plane of incidence strong TM to TE conversion occurs and for the optimum depth grating over 50% conversion is readily achieved. Thus devices may be based on the principle of detecting a large signal on a weak background and monitoring this change in signal.

If we modulate the source then we can detect at the modulation frequency increasing the signal to noise ratio.

The extra momentum required to couple photons directly to a surface plasmon-polariton at a metal/air boundary may be provided by the SPP-carrying surface being a grating because a grating, if rotated out of the plane of incidence, is also capable of converting p (TM) radiation into s (TE) radiation then the SPP may be coupled to, with suitable choice of grating orientation by any polarisation. The strength of coupling to the SPP has been studied as a function of $\phi$, the angle between the normal to the plane of incidence and the grating grooves, using a photoacoustic technique. Because of symmetry constraints, at $\phi=0$ only p-polarised light couples to the SPP while at $\phi=\pi/2$ only s-polarised light is coupled.

In the present example the p to s conversion, through generation of the SPP is examined as $\phi$ is changed from 0 to $\pi/2$. For these two limits no p-s conversion occurs while at $\phi=45°$ conversion as high as 66% is possible. This p-s conversion has previously been recorded in planar systems with tilted uniaxial or biaxial layers and utilised to fully characterise the optic tensor through the study of guided modes. Symmetry breaking is provided by the grating grooves as opposed to the out of plane optical axis. With conventional optical studies of SPP resonances a minimum in reflectivity is recorded at the plasmon angle, but we record a maximum.

BRIEF DESCRIPTION OF THE DRAWINGS

The invention will now be particularly described with reference to the accompanying drawings, in which:

FIGS. 9a and 9b show alternative embodiments of the invention for use as a gas detector;

FIGS. 10a and 9b illustrates the use of a long range surface plasmon in gas chromatography;

FIG. 11 shows an SPP-based voltage-controlled monochromator;

FIG. 12 shows an alternative form of voltage-controlled monochromator;

FIG. 13 is an optical reader for magnetic tape.

DESCRIPTION OF THE PREFERRED EMBODIMENTS

Gratings were produced using a holographic technique. Clean glass discs were spin-coated with photoresist (Shipley 1400-17) and baked at 60° C. for 30 minutes. These coated discs were then exposed to two intersecting coherent beams from an argon ion laser (457.9 nm) for a range of exposure times. After exposure the films were developed, rinsed and left under an ultra-violet lamp for 30 minutes to harden the photoresist fully. Groove depths were subsequently measured using a Talystep stylus measuring instrument.

Such gratings were stored in a clean environment until, when needed, they were placed in a vacuum chamber for coating with an appropriate metal layer. Opaque silver layers of about 100 nm thickness were deposited by evaporation of 99.999% pure silver in a vacuum of $10^{-4}$ Pa. The pitch, $\lambda_g$, of the gratings used was determined by the angles of the diffracted orders, and in all the gratings used here was 842.5±0.5 nm.

Figure 1:
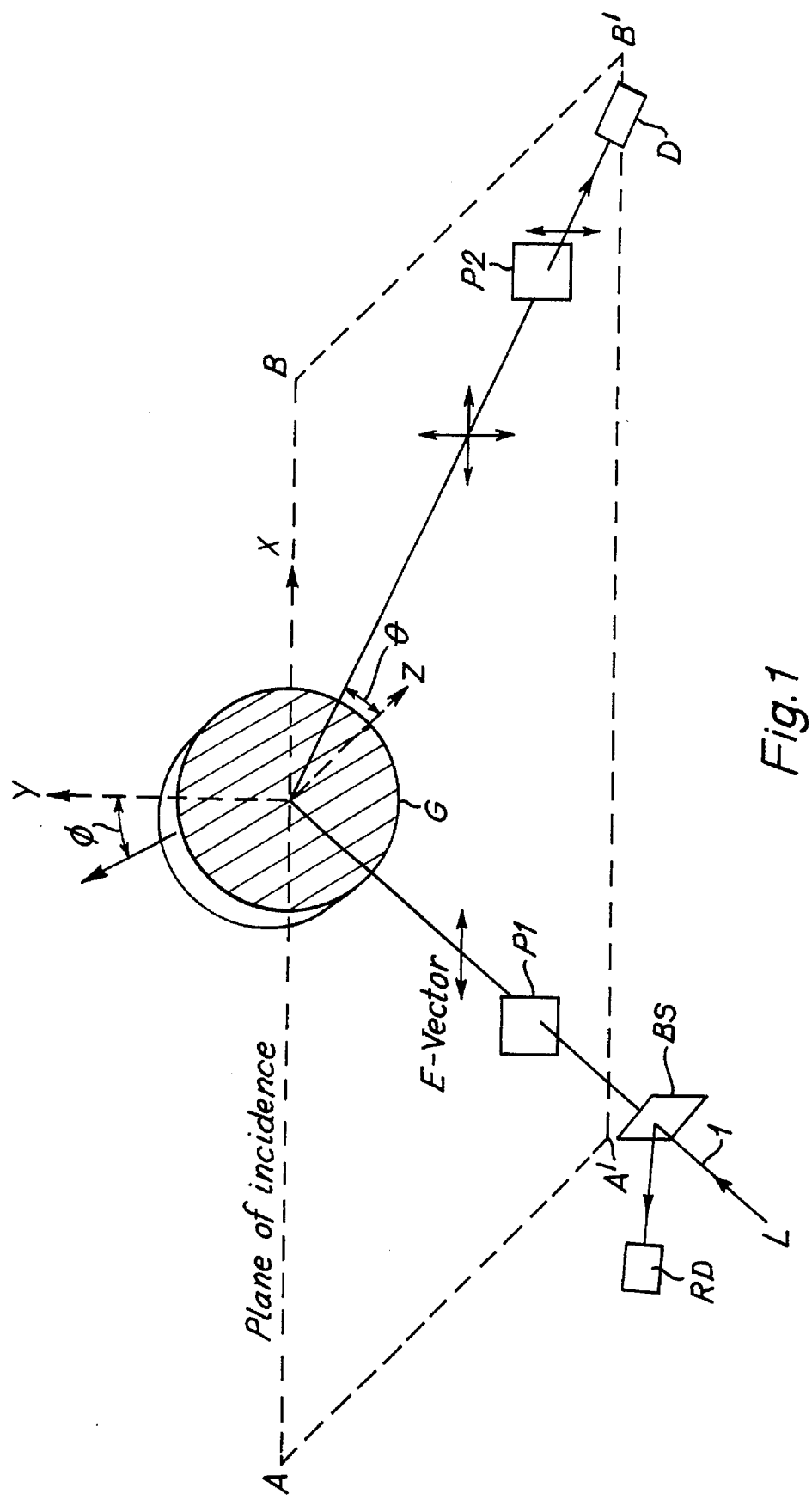
FIG. 1 is a schematic diagram of apparatus used to obtain measurements on SPPs.

The experimental arrangement used to monitor the reflecting properties of these metallised gratings is shown schematically in FIG. 1. Gratings G were mounted on a table (not shown) that allowed angle ($\theta$) scans having 0.01° step resolution. The azimuthal angle $\phi$ could be set to an accuracy of ±0.1°. P-polarised (TM) HeNe laser radiation L ($\lambda=632.8$ nm) was mechanically chopped at 1.7 KHz and then directed onto the grating through a beam splitter BS and polariser P1. The zeroth order (specular beam) from the grating G was detected with a photodiode (rotating at twice the rate of the grating) and a lock-in amplifier after passing through a second polariser P2 set to pass the s-component of the beam. The extinction ratio of the two polarisers was greater than 200,000:1. A reference detector RD monitored the input beam through a 4% reflection off a glass plate beam splitter BS placed in the beam. This reference signal was used to correct the output signal for any fluctuations in input intensity. $R_{ps}$ was measured as a function of $\theta$ with the scans being repeated for different $\phi$ values. Absolute magnitudes of $R_{ps}$ were obtained by measuring the input beam with the signal detector set for p-polarisation. To reduce the influence of overlayer contamination of the Ag film the reflectivity measurements were conducted within 30 minutes of the deposition of the silver.

Figure 2:
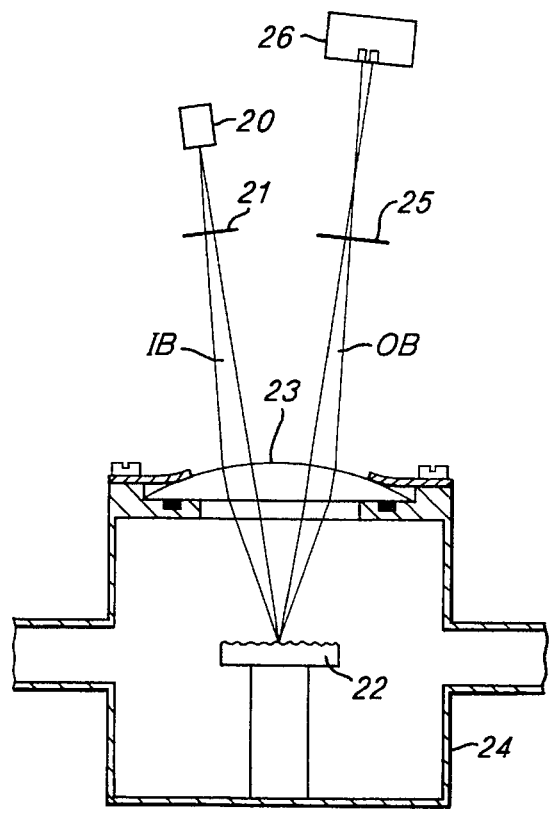
FIG. 2 shows a prototype for detection of the angle of the SPP maximum using a divergent source and a split detector.

FIG. 2 shows a practical embodiment of the apparatus. A CW laser diode 20 acts as a radiation source for an input beam IB which passes through a TM polariser 21 and is focused onto a grating 22 by a glass lens 23 which serves as a window to a sample chamber 24. An output beam OB passes through the lens 23 and a TE polariser 25 to a split detector 26 which resolves the angular position of the maximum. The grating pitch is designed to give SPP at ~10° incidence.

Figure 3:
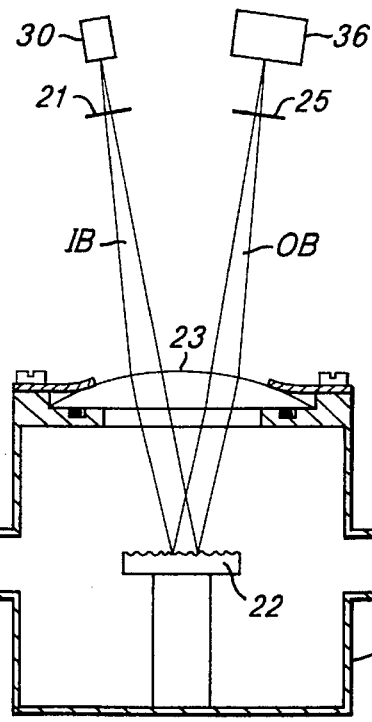
FIG. 3 shows a prototype for detection of the wavelength of the SPP maximum using a polychromatic source and a split wavelength detector.

FIG. 3 is another form of apparatus, using a light-emitting diode 30 in place of the laser of FIG. 2. The wavelength spread of the LED is ≈±50 nm. The detector 36 is a split wavelength detector with two diodes of different wavelength response. The output is very linear in position of wavelengths maximum. The grating pitch is designed to give SPP at ~10° incidence.

Figure 4:
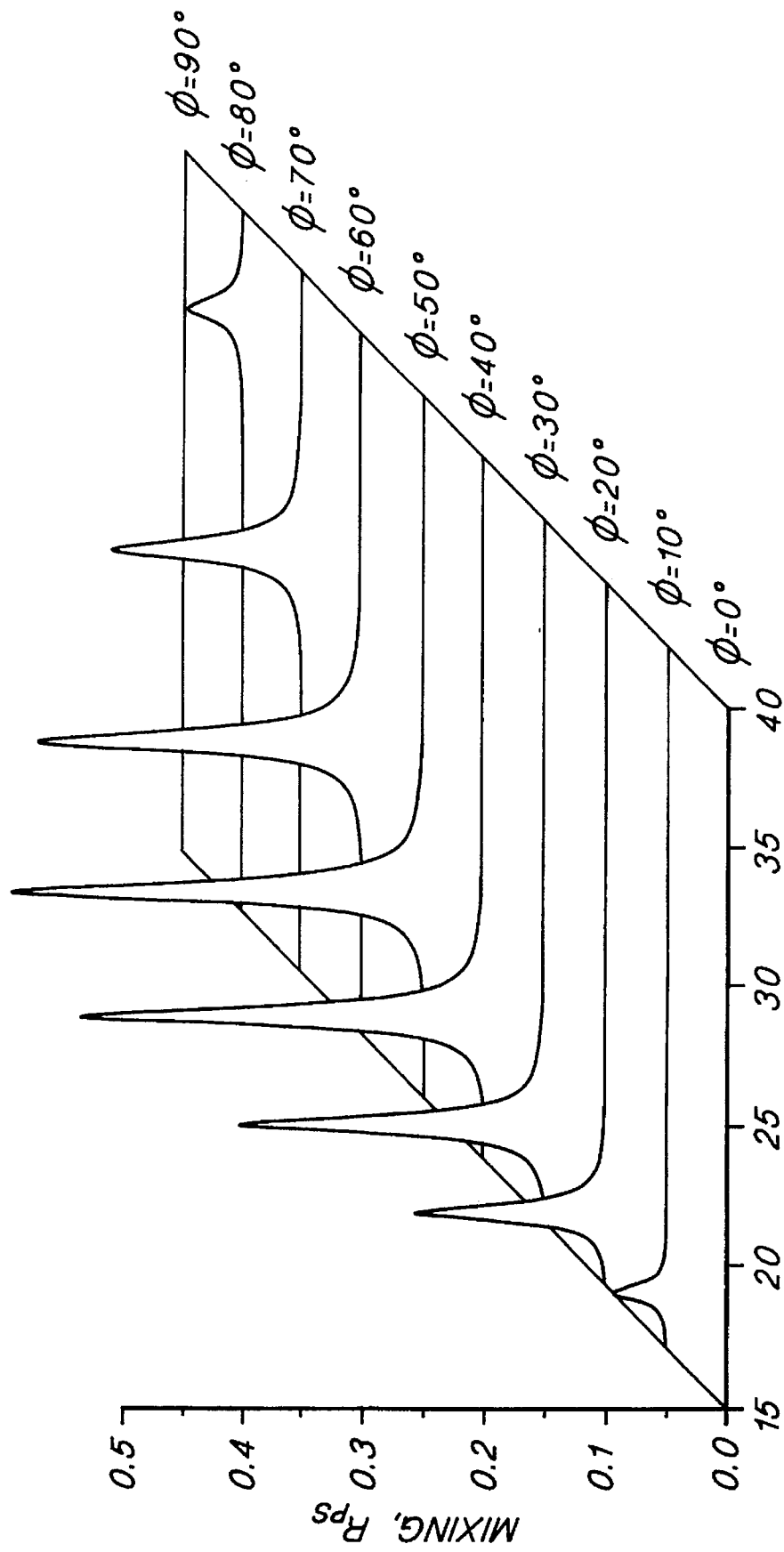
FIG. 4 shows p to s coupling, $R_{ps}$ as a function of angle of incidence at different $\phi$ for a grating with groove depth of 55.4 nm.

FIG. 4 shows results taken with the apparatus of FIG. 3. When small amounts of isopropanol (<1 Torr) are added to the chamber, condensation occurs on the metal surface and causes a change in the output of the wavelength detector. Pumping out the chamber re-evaporates the liquid and returns the surface to its original conditions.

Figure 5:
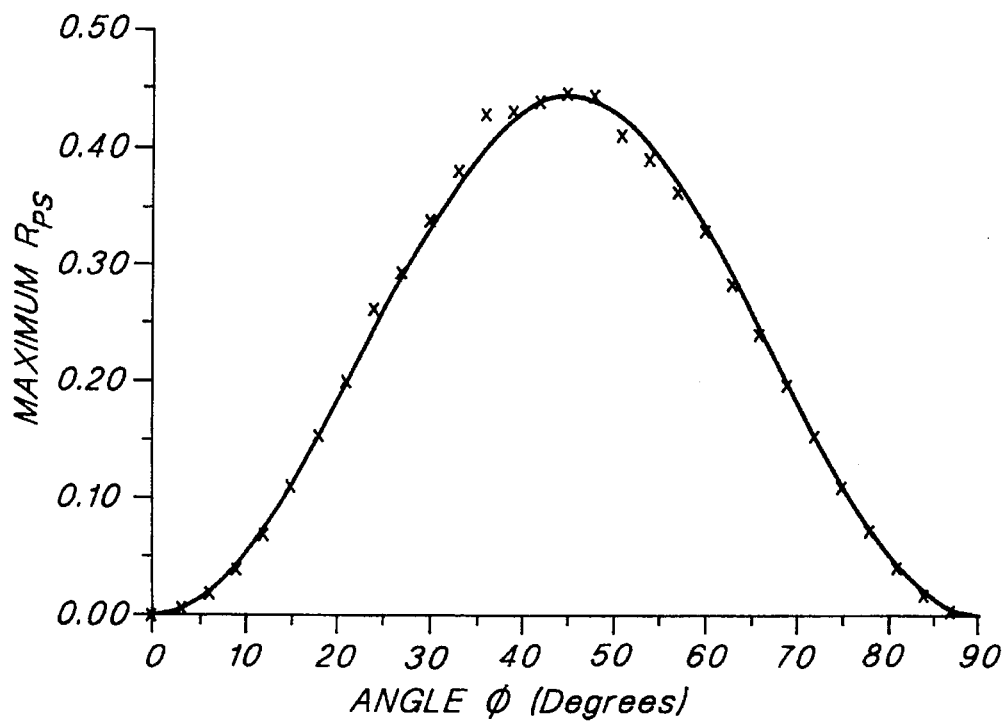
FIG. 5 shows $R_{ps}$ peak height as a function of angle $\phi$ for a grating with groove depth of 55.4 nm.

Reflectivity data in the form $R_{ps}$ against $\theta_{spp}$ were recorded for ten different gratings, each with the same pitch but having different groove depths. FIG. 4 illustrates the results recorded and this particular set of data is for a grating with a groove depth of 55.4 nm. For $\phi=0°$ and 90°, i.e. grooves perpendicular or parallel to the plane of incidence, there is no detected $R_{ps}$. For all intermediate $\phi$ values there is a resonance peak at an angle of incidence which corresponds to the excitation of a surface plasmon, $\theta_{spp}$. The movement of $\theta_{spp}$ with $\phi$ is clearly visible. FIG. 5 shows the variation of the $R_{ps}$ peak height with $\phi$. The maximum p to s conversion occurs at $\phi=45°$ with, for this grating, almost 45% of the p radiation being converted through SPP absorption and re-radiation into s radiation. The $\phi$ dependent data closely follows a simple $\sin^2\phi.\cos^2\phi$ ($=\sin^2 2\phi$) solid line dependence which is readily explained in terms of the electric-field components. P-polarised incident radiation has an E-vector component perpendicular to the grooves which varies as $\cos\phi$. This in turn has a component perpendicular to the incident vector which varies as $\sin\phi$. The product of these components is then squared to give the intensity.

Figure 6:
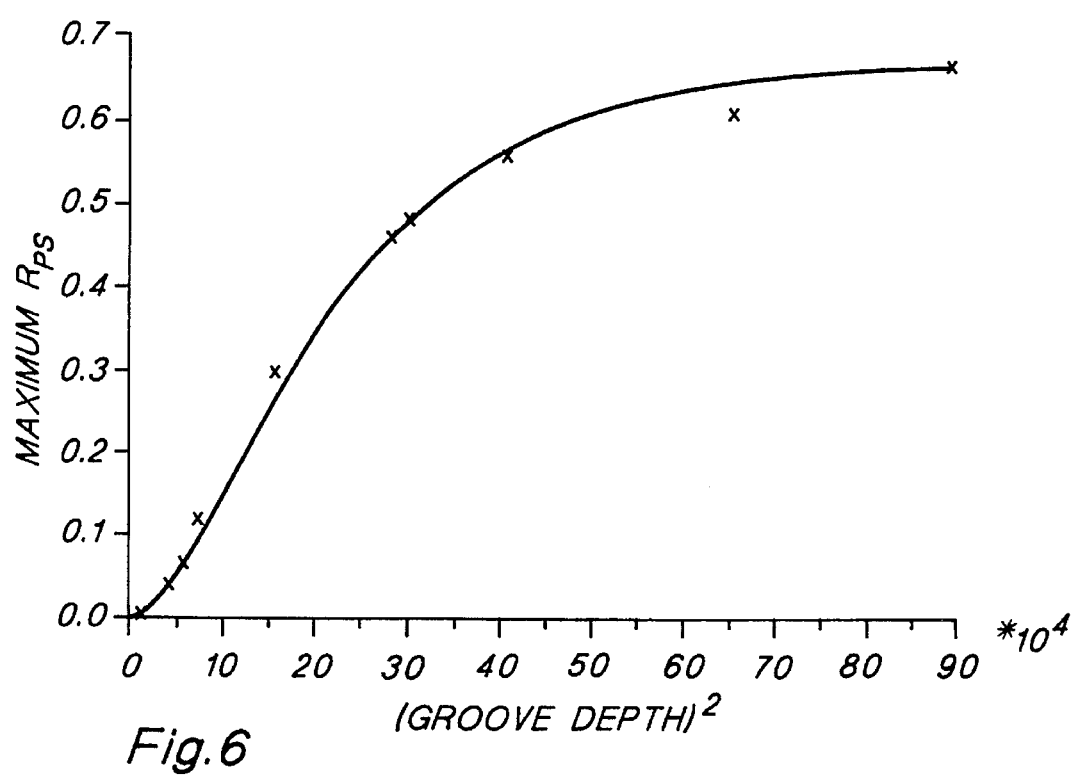
FIG. 6 shows maximum $R_{ps}$ (at $\phi=45°$) as a function of groove depth.

For all the gratings, the maximum $R_{ps}$ at $\phi=45°$ was determined and the results, plotted against the square of the groove depth, are shown in FIG. 6. The maximum conversion recorded was about 66% from a grating with an amplitude of 94.7 nm. (By contrast, a polariser placed at angle $\phi$ between two crossed polarisers gives a maximum 12.5% conversion having likewise a $\sin^2 2\phi$ intensity dependence). The solid line shown in FIG. 6 is a curve of the form;

$$R_{ps}(max)=A[1-\exp(-Bh^2)]^2. \tag{1}$$

Figure 7:
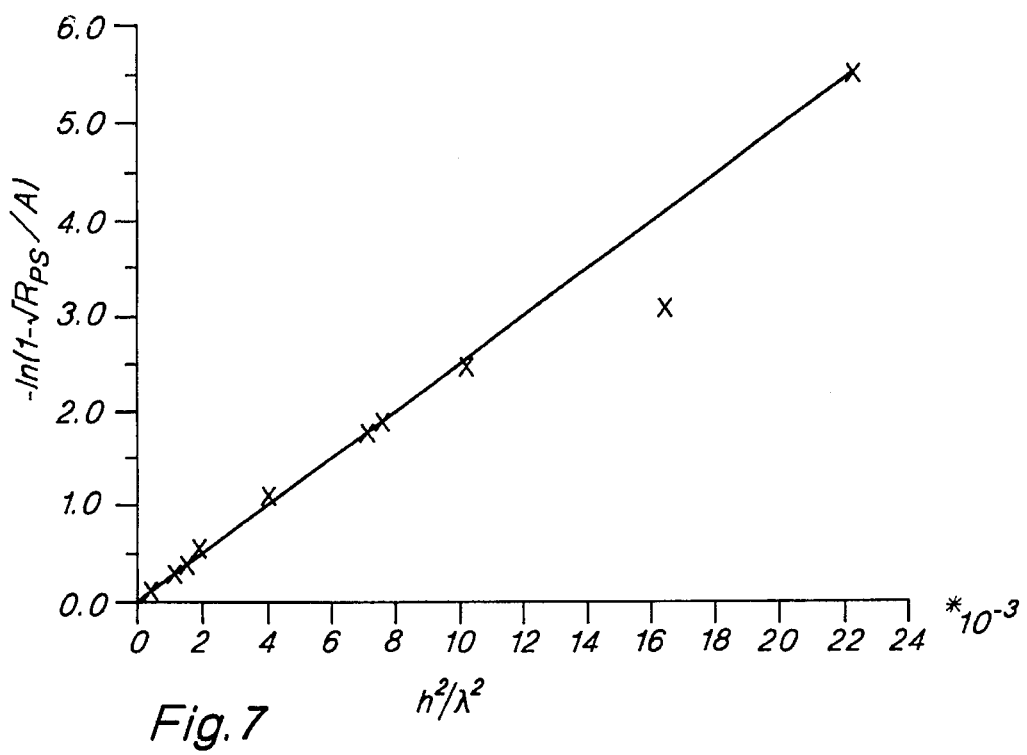
FIG. 7 shows a straight line fit to equation 1.

The coefficients A and B are determined to be ⅔ and $(251\pm10)/\lambda^2$ respectively (B is indistinguishable from $8\pi^3/\pi^2$). The straight line fit of $\ln(1-(R_{ps}/A)^{1/2})$ against $(h/\lambda)^2$ for these values of A and B is shown in FIG. 7.

In measurements of p to s conversion through the coupling of radiation to an SPP wave on a metallised grating, the dependence of the conversion efficiency on the groove depth and on the angle between the grating groove direction and the plane of incidence both take a very simple empirical form with a maximum conversion efficiency of ⅔ for the deepest grating.

By SPP conversion, the grating is acting as a specular monochromator. That is, if p-polarised parallel white light is shone onto the grating at $\phi=45°$, the reflected beam when viewed through a second polariser will have a color depending purely on $\theta$. The narrower the SPP resonance the sharper the wavelength resolution in the output beam, the color being dictated by that of the SPP mode on the metal surface. However to give strong conversion, it is necessary to use a large groove depth which substantially broadens the SPP resonance and thereby limits the resolution.

Figure 8:
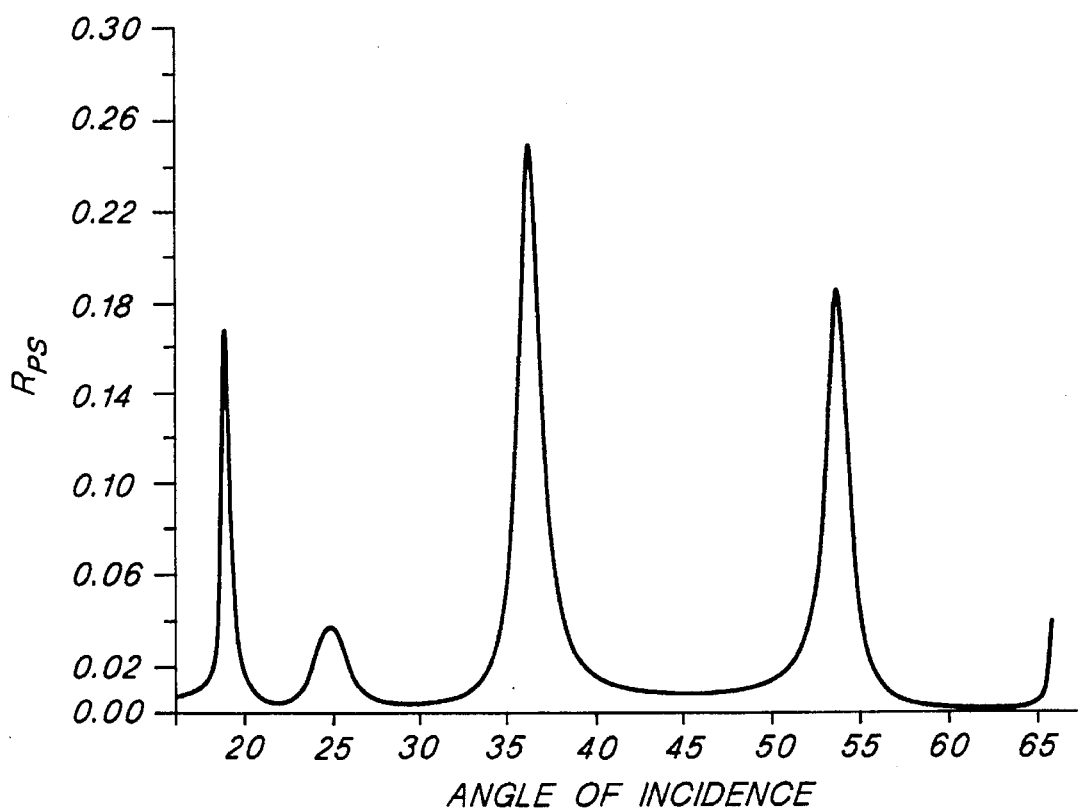
FIG. 8 shows application of the invention using a guided mode.
Figure 14:
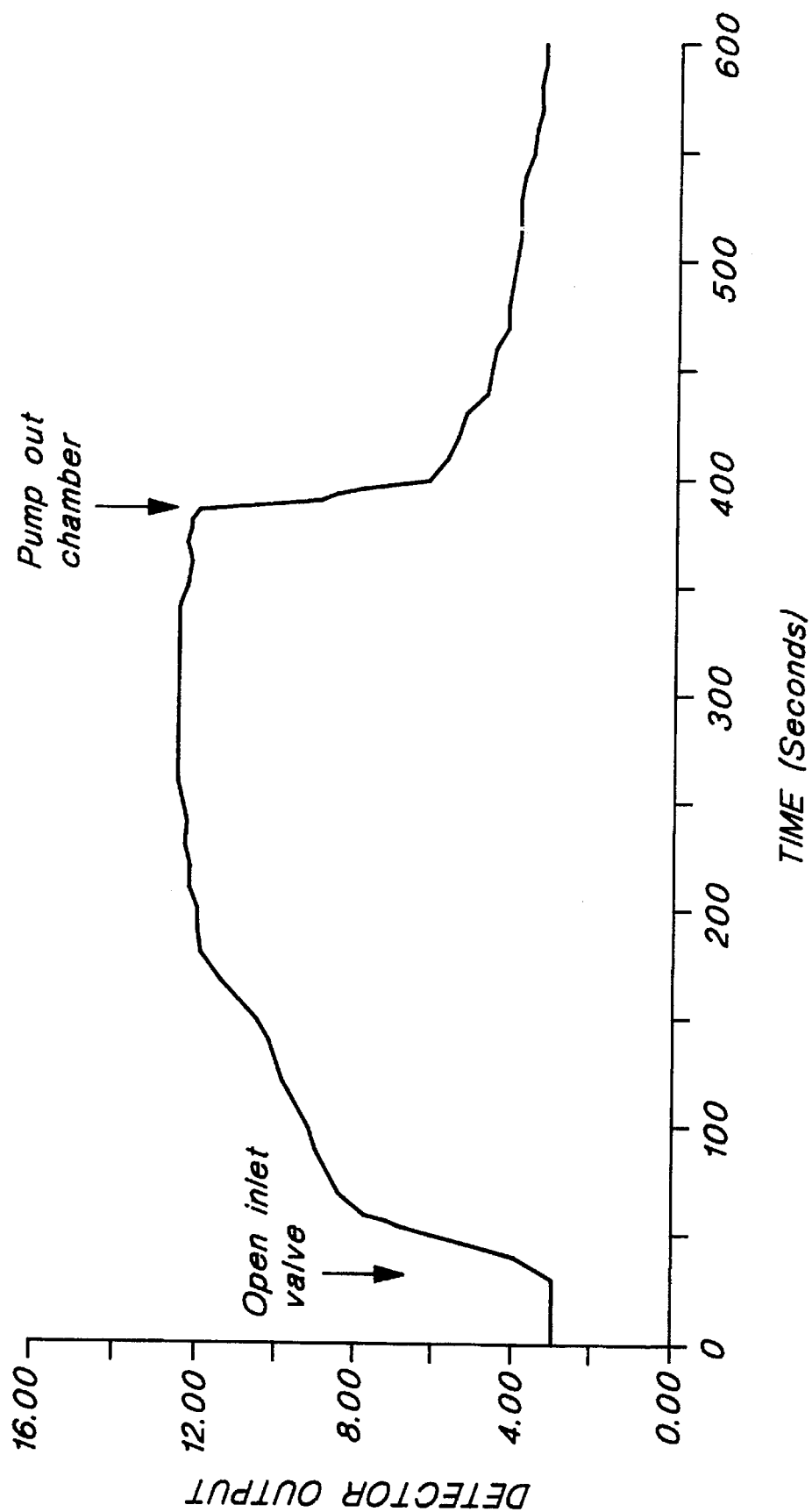
FIG. 14 is an optical reader for magnetic information taken with the apparatus of FIG. 3.

Guided modes in a dielectric overlayer will also couple p to s on a grating. FIG. 8 shows $R_{ps}$ data taken at $\phi=45°$. The sample is a silver coated grating similar to that used in the previous example (groove depth of 53.6 nm) but with a thin layer of photoresist spun on the silver. The modes give significant p to s coupling and, by careful overlayer application, modes as narrow as 0.1° HHFW should be obtainable.

Two broad types of devices may be based on the principle of the surface plasmon. These are:

(a) Devices based on momentum spread at fixed wavelength, and (b) Devices based on wavelength spread at fixed momentum.

For the former, one needs a monochromatic source—possibly a laser diode—and a position sensor.

For the latter one needs—a polychromatic source—possibly an LED and a wavelength sensor (dual diode detector).

There are two further subdivisions into:

(1) Metallised gratings supporting surface plasmons, and (2) Gratings coated with a dielectric layer supporting guided modes.

The first category will be sensitive to thin overcoatings and may themselves be overcoated with sensing layers.

The second category will be sensitive to changes in the optical properties of the dielectric layers.

An embodiment of the invention which serves as a gas sensor is shown in FIGS. 9a and 9b. This comprises a substrate 90 having a grating coated with a layer of gold 91 bearing a Langmuir-Blodgett (LB) film 92. Gas G flows over the film. The grating is alternatively illuminated with an incident beam IB comprising monochromatic light with an angular spread (FIG. 9a) or collimated polychromatic light. The device acts as a gas sensor due to absorption of gas by the LB film—this changes the SPP resonance which is detected.

The use of a long range surface plasmon (LRSP) in gas chromatography is shown in FIG. 10. Gas enters the porous layer 101 bearing a gold layer 102 and changes the dielectric constant $\epsilon$ locally. This is seen as an image in an s detected signal.

FIG. 11 shows one form of voltage-controlled monochromator based on an SPP. An incident beam IB of white light is directed onto a grating coated with a transparent indium-tin oxide layer 111. This in turn, bears a layer 112 of a voltage sensitive polymer which is coated with gold or silver 113. A voltage change across the polymer applied by a voltage source 114 will cause a change in dielectric constant $\epsilon$ which leads to a color change in the s output. Conversion efficiency is of the order of 60%. Spectral resolution is dictated by collimation of beams and sharpness of resonance.

FIG. 12A shows an alternative embodiment of a voltage-controlled monochromator, but uses a liquid crystal layer positioned between the surface plasmon grating and a glass plate 121 bearing an indium tin oxide layer and a silica layer 122 aligned as shown in FIG. 12b.

FIG. 13 shows an optical reader for magnetic information using an LRSP comprising a silica substrate 130 and a gold grating overlayer 131 with a magnetic overlayer 132. The field from a tape 133 realigns magnetic overlayer and changes the LRSP. Hence magnetic information is converted directly to optical information. A plastic coating 134 for the magnetic overlayer acts as spacer and lubricant for tape flow.

Conversion of p to s radiation can also occur via guided modes in dielectric overlayers on a metallised grating. FIG. 15 shows $R_{pp}$ and $R_{ss}$ reflectivities (at $\phi=0$) from a sample consisting of 320 nm of magnesium fluoride on 100 nm of silver, evaporated under the same vacuum on to a grating (pitch=801.5 nm, depth=21.1 nm). The $R_{pp}$ plot shows the SPP (at ~42°) and the $TM_o$ (lowest order transverse magnetic) guided mode (at ~13°). The guided mode is narrower than the SPP mode as most of its field is in the non-absorbing dielectric. The $R_{ss}$ plot shows the $TE_o$ guided mode.

Figure 16:
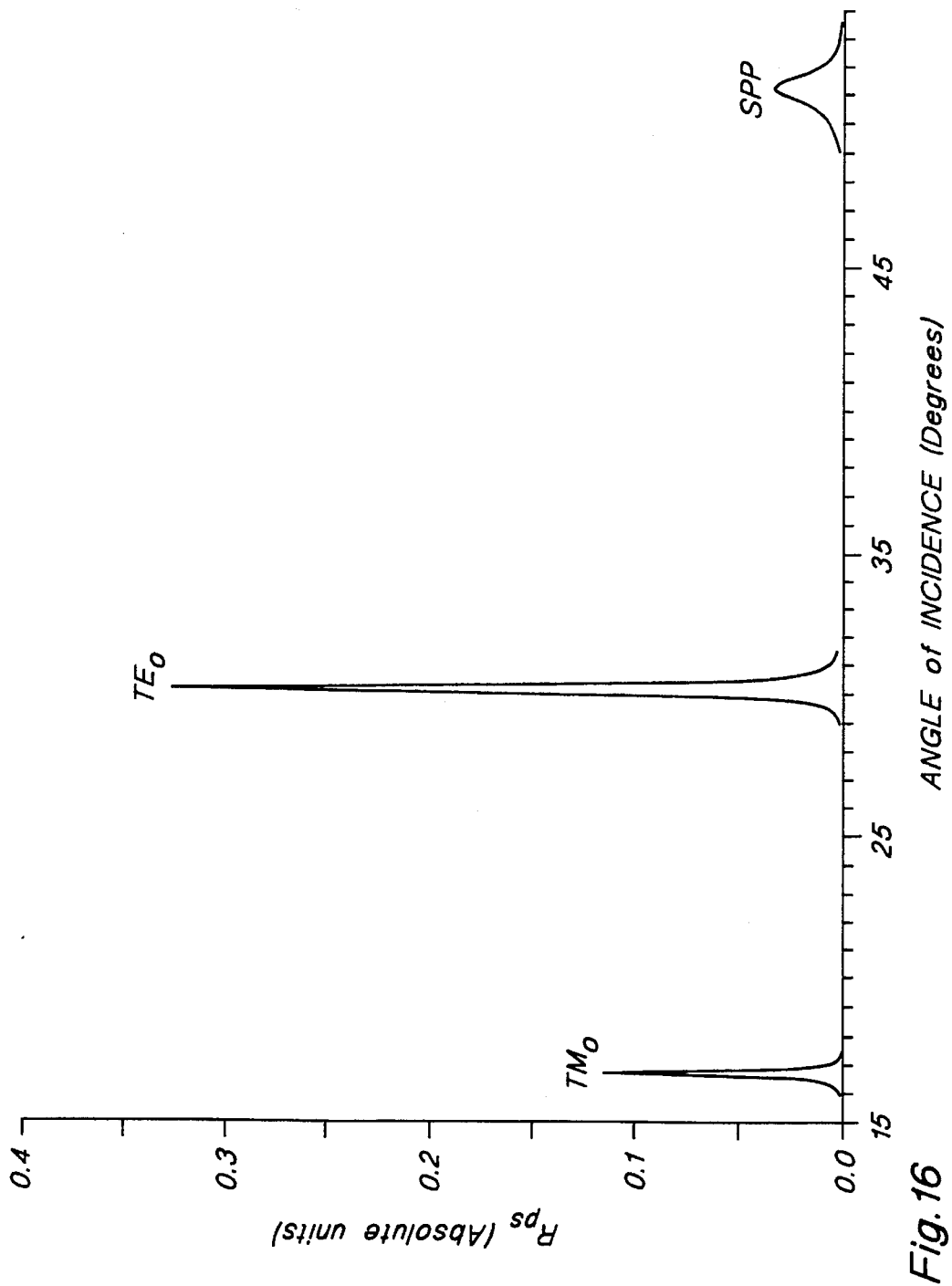
FIG. 16 shows the peak heights for the guided mode for $\phi=0°$ to 90°.
Figure 15A:
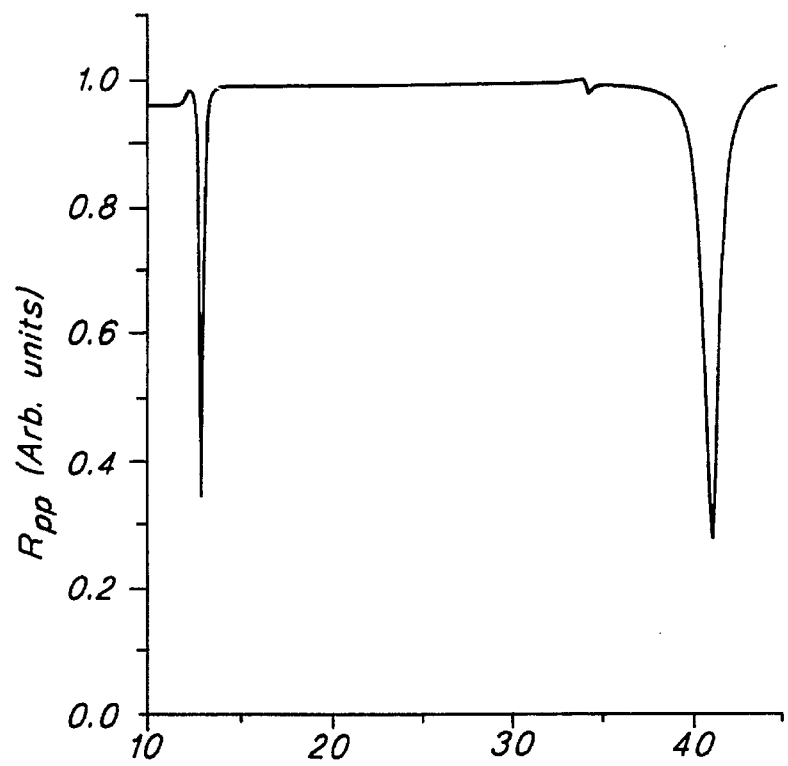
FIG. 15a and 15b are $R_{sp}$ plots wherein the grating is rotated to $\phi=45°$.
Figure 15B:
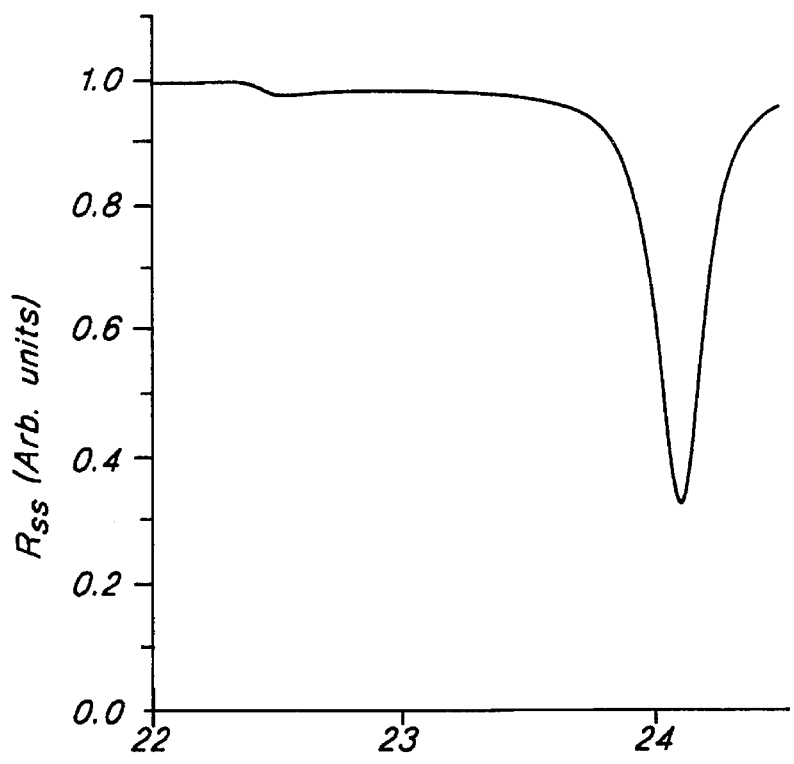
Figure 17:
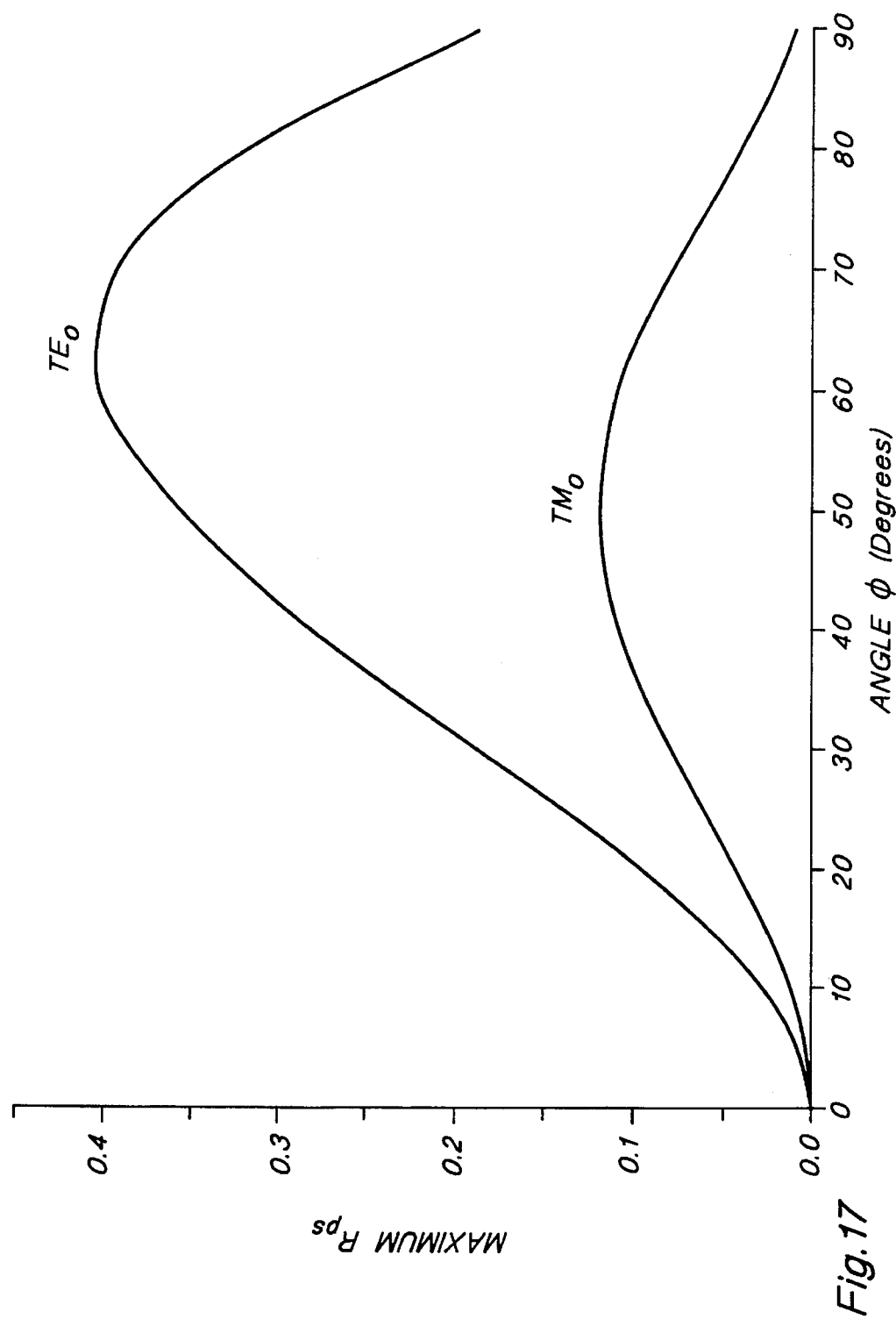
FIG. 17 shows the maximum $R_{ps}$ for $\phi=0°$ to 90°.
Figure 18:
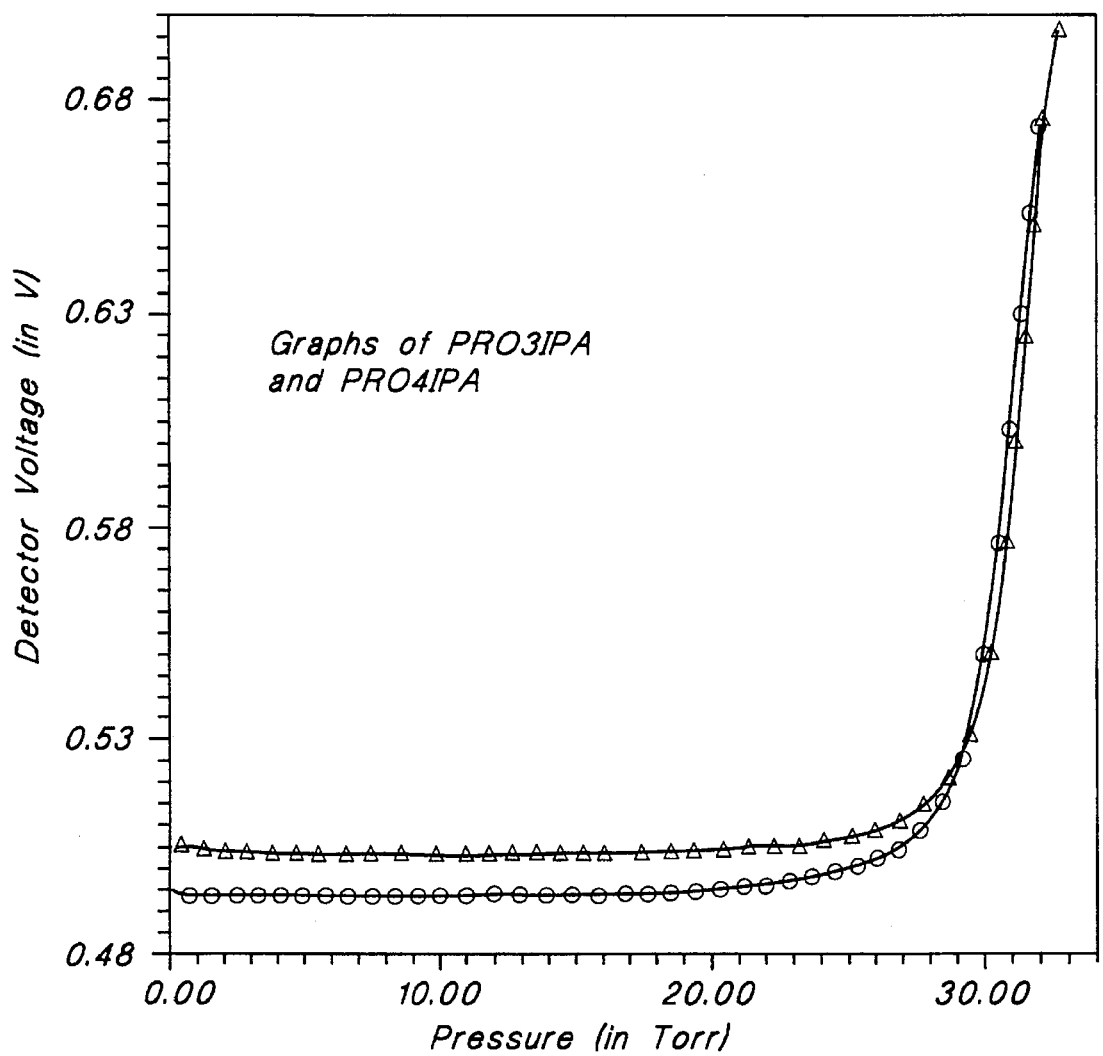
FIG. 18 is a graph showing detector voltage versus pressure for PRO3IPA and PRO4IPA.
Figure 19:
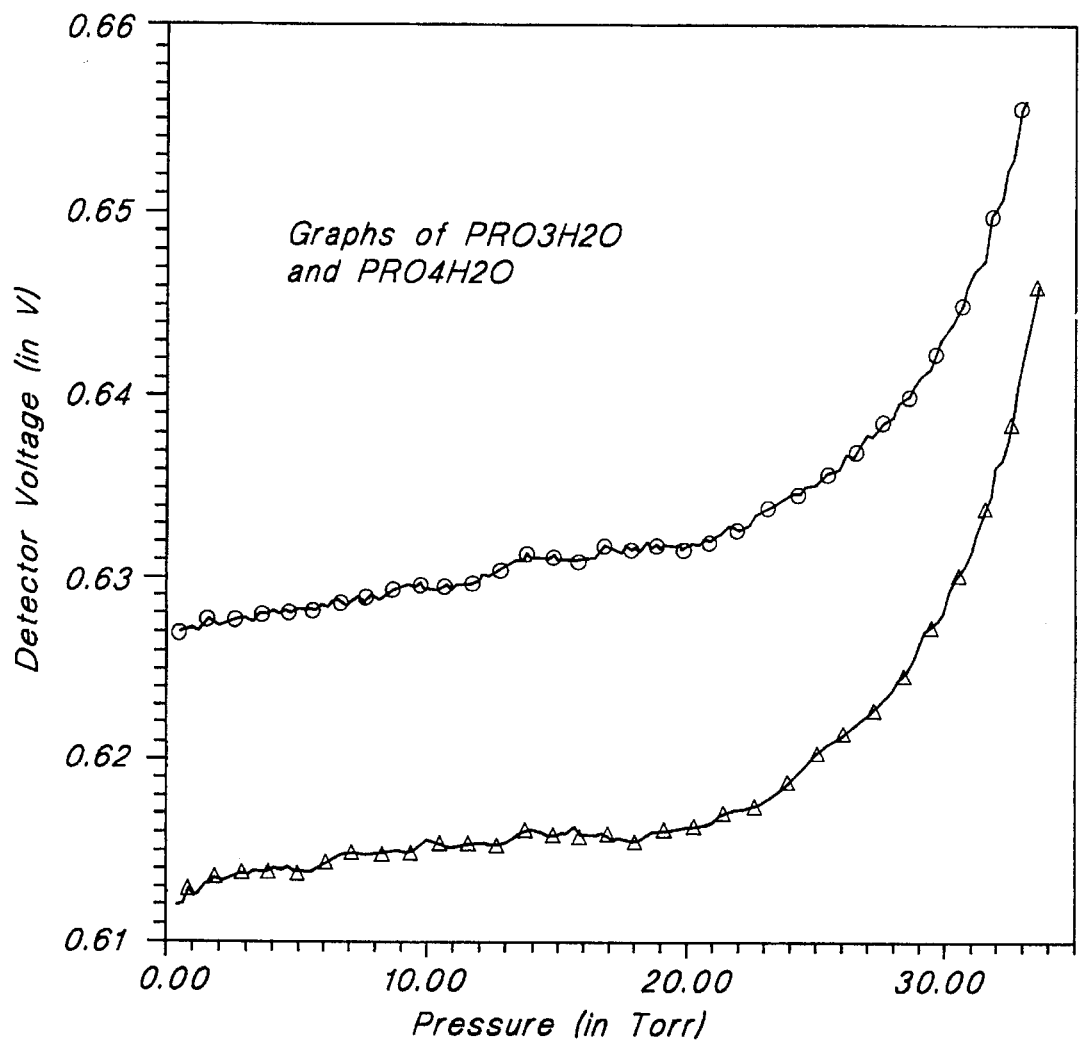
FIG. 19 is a graph showing detector voltage versus pressure for PRO3H20 and PRO4H20.
Figure 20:
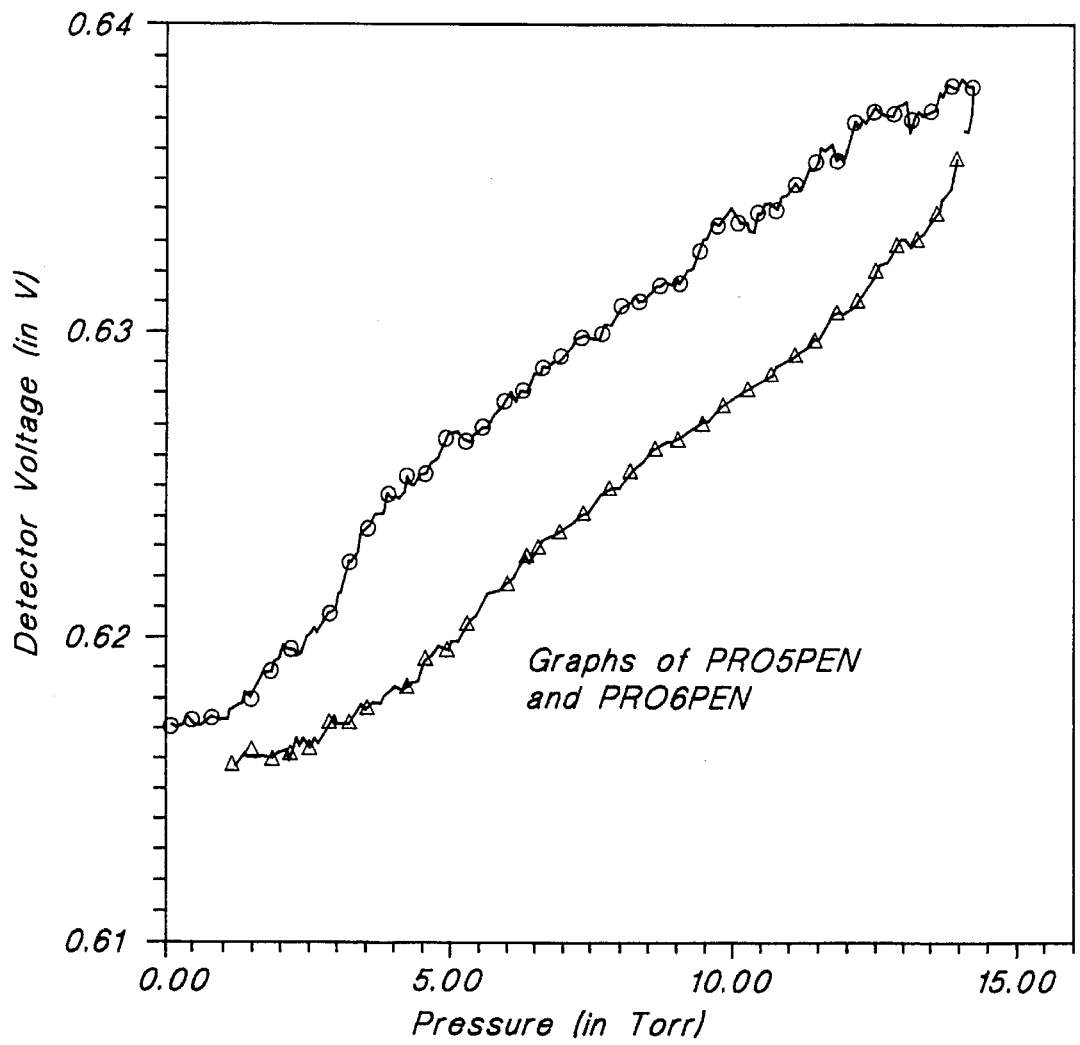
FIG. 20 is a graph showing detector voltage versus pressure for PRO5PEN and PRO6PEN.
Figure 21:
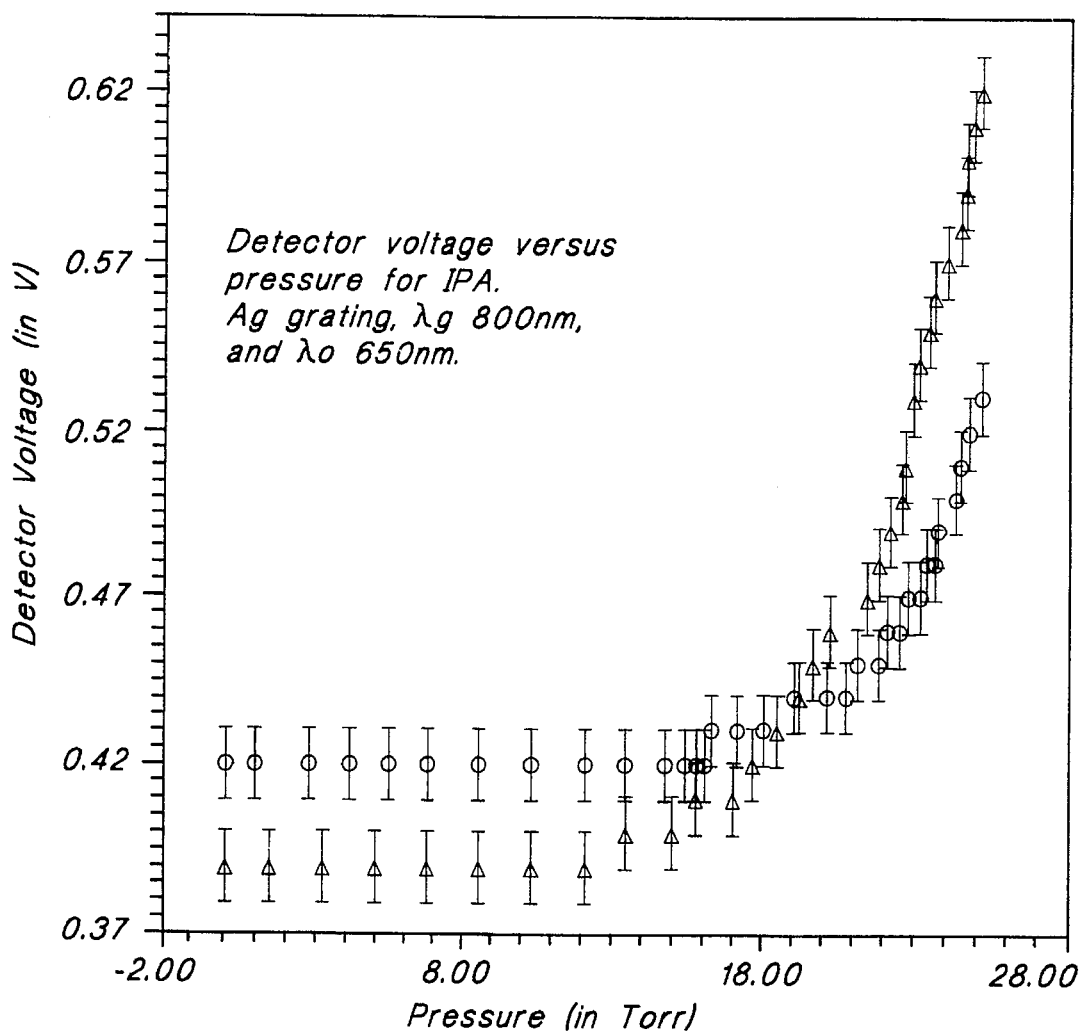
FIG. 21 is a graph showing detector voltage versus pressure for IPA where the Ag grating is 800 nm and 650 nm.
Figure 22:
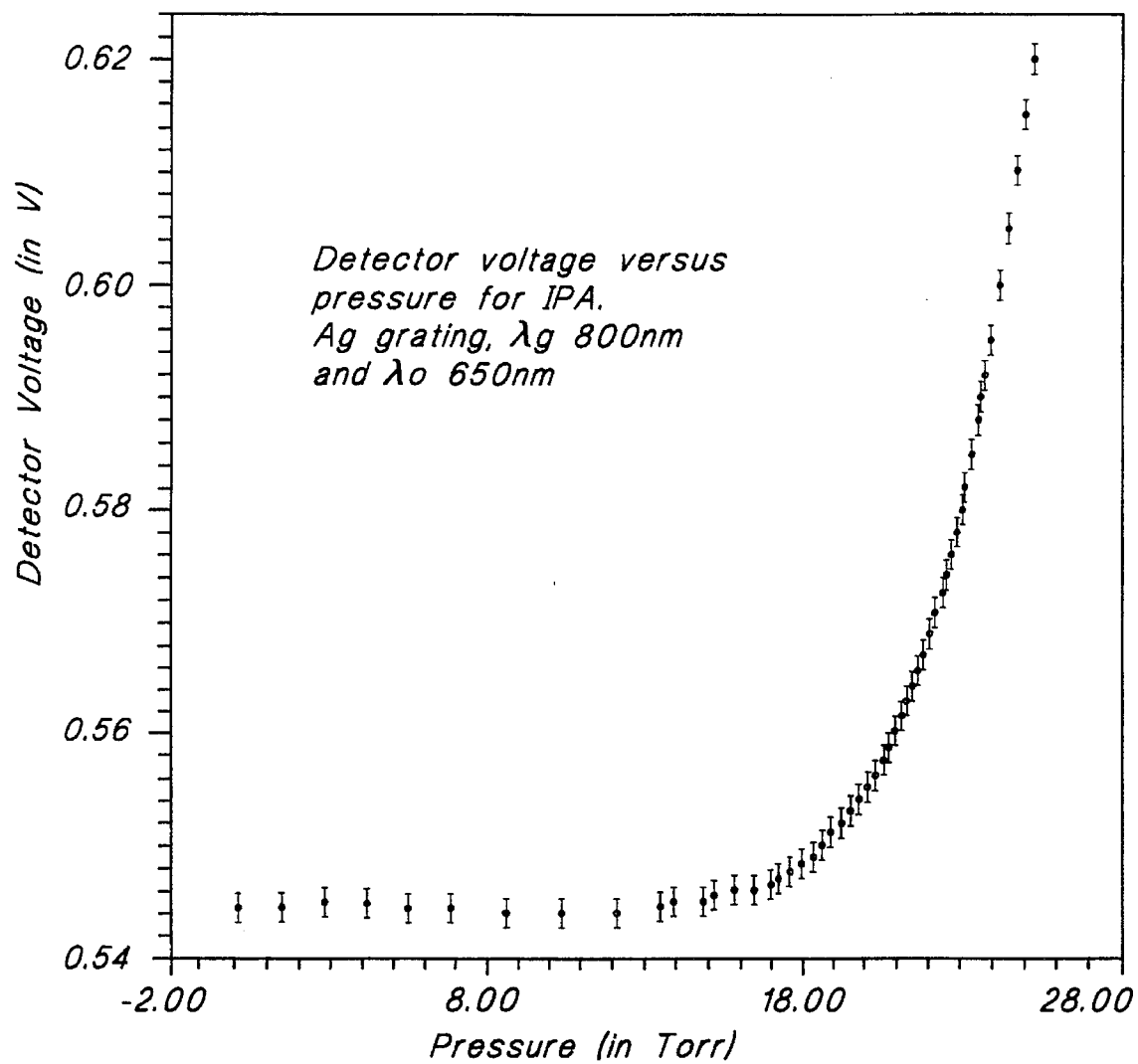
FIG. 22 is a graph showing detector voltage versus pressure for IPA where the Ag grating is 800 nm and 650 nm.

If the grating is rotated to $\phi=45°$, we obtain the $R_{sp}$ plot shown in FIG. 15A and 15B. The guided modes show much bigger mixing than the SPP. All the modes have moved to a higher angle in a similar way to the SPP in FIG. 4. By measuring the peak height for the guided modes for $\phi=0°$ to 90° we obtain the curves in FIG. 16. These curves for the guided modes differ from FIG. 5 (for the SPP) in two important respects. The maximum of each curve is now at $\phi>45°$ and they are both non-zero at $\phi=90°$. The same layers were also deposited on two other gratings of identical pitch but different groove depths. Table 1 shows the peak heights for the two guided modes and also the SPP for all three gratings at $\phi=45°$. (For the guided modes, this is not the optimal $\phi$). The SPP mixing is compatible with the previous results for gratings coated only with silver.

These results show that guided modes provide much larger mixing than SPPs especially for small groove depths. They are also narrower and hence will allow greater sensitivity in detecting mode shifts. With a dielectric coating on a metallised grating, the detectors shown in FIGS. 2 and 3 would now be sensitive to refractive index and thickness changes in the coating. The choice of layer would determine what materials are to be sensed. For example, layers exist that are only sensitive to specific gases and antibody layers exist that will only combine with the corresponding antigens. In both cases mainly the refractive index of the layer is modified.

TABLE 1

| | Mixing at 45° | | |
|---|---|---|---|
| Groove depth (nm) | $TM_O$ | $TE_O$ | SPP |
| 211 | 0.115 | 0.326 | 0.033 |
| 376 | 0.359 | 0.496 | 0.159 |
| 719 | 0.508 | 0.559 | 0.277 |

We claim:

1. An apparatus for sensing polarization conversion in a coating layer on a diffraction grating having grating lines lying in a grating plane, said apparatus comprising:

means for illuminating the coating with radiation at a first polarization, the direction of said first polarization and the direction of the grating lines being disposed at an angle with respect to one another in the grating plane, said angle being greater than 0° and less than 90°;

means for receiving radiation reflected by the coating layer at a second polarization, said first polarization and said second polarization being disposed in radiation paths that are crossed with respect to one another; and means for sensing a maximum of received radiation reflected by the coating layer.

2. An apparatus according to claim 1 in which the polarization conversion is effectuated by surface plasmon polariton resonance.

3. An apparatus according to claim 2 in which the coating layer comprises a metal coating.

4. An apparatus according to claim 3 in which the angle at which the direction of the first polarization and the direction of the grating lines are disposed with respect to one another is 45°.

5. An apparatus according to claim 4 in which the means for illuminating the coating comprises a monochromatic source, and the means for receiving radiation is sensitive to the angular position of the received radiation.

6. An apparatus according to claim 5 in which the radiation from the monochromatic source is focused on the coating layer.

7. An apparatus according to claim 6 in which the monochromatic source is a laser diode.

8. An apparatus according to claim 5 in which the means for receiving radiation is a plurality of spaced radiation sensors.

9. An apparatus according to claim 4 in which the means for illuminating the coating comprises a polychromatic source, and the means for receiving radiation is wavelength sensitive.

10. An apparatus according to claim 9 in which the radiation from the polychromatic source is arranged to illuminate the grating with a collimated beam.

11. An apparatus according to claim 9 in which the polychromatic source is a light emitting diode.

12. An apparatus according to claim 9 in which the wavelength sensitive means for receiving radiation comprises a dual diode detector.

13. An apparatus according to claim 4 further comprising means for varying a property of the coating layer on the diffraction grating whereby surface plasmon resonance occurs.

14. An apparatus according to claim 13 further comprising a fluid-tight container surrounding the diffraction grating, and means for causing a fluid to flow past the diffraction grating.

15. An apparatus according to claim 14 in which the fluid is a vapor.

16. An apparatus according to claim 14 in which the fluid is a gas.

17. An apparatus according to claim 3 in which the metal coating is gold.

18. An apparatus according to claim 3 in which the metal coating is silver.

19. An apparatus according to claim 3 in which the metal coating is indium-tin oxide.

20. An apparatus according to claim 3 in which the metal coating overlies a porous layer.

21. An apparatus according to claim 3 in which the metal coating overlies a voltage sensitive polymer layer.

22. An apparatus according to claim 3 in which the metal coating overlies a magnetic layer.

23. An apparatus according to claim 3 in which the metal coating is illuminated at a metal-atmosphere interface.

24. An apparatus according to claim 23 in which the metal coating is gold covering a porous layer and the apparatus comprises a gas chromatograph.

25. An apparatus according to claim 3 in which the metal coating is illuminated at a metal-substrate interface.

26. An apparatus according to claim 25 in which the metal coating is indium-tin oxide covering a layer of voltage sensitive polymer to enable the apparatus to function as a voltage controlled monochromator.

27. An apparatus according to claim 25 in which the metal coating is gold covering a layer of magnetic overlay to enable the apparatus to function as a reader of magnetic information.

28. An apparatus according to claim 1 in which the coating layer is gold covered with a Langmuir-Blodgett film to enable the apparatus to function as a gas sensor.

29. An apparatus according to claim 1 in which the polarization conversion is caused by a guided mode.

30. An apparatus according to claim 29 in which the coating layer is a dielectric layer.

31. An apparatus according to claim 30 in which said angle is greater than 45°.

32. An apparatus according to claim 31 in which said angle is between 50° and 60°.

33. An apparatus according to claim 31 in which the means for illuminating the coating comprises a monochromatic source, and wherein the means for receiving radiation is sensitive to the angular position of the received radiation.

34. An apparatus according to claim 31 in which the means for illuminating the coating comprises a polychromatic source, and the means for receiving radiation is wavelength sensitive.

35. An apparatus according to claim 31 in which the dielectric layer is sensitive to a specific gas and the apparatus functions as a gas detector.

36. An apparatus according to claim 31 in which the dielectric layer is a layer of an antibody and the apparatus functions as a detector of the corresponding antigen.

37. An apparatus according to claim 30 in which the dielectric layer overlies a metal layer.

38. An apparatus according to claim 30 in which the dielectric layer comprises a photoresist material.

39. An apparatus according to claim 30 in which the dielectric layer comprises magnesium fluoride.

* * * * *